US00PP27218P3

(12) United States Plant Patent
Tellwright

(10) Patent No.: US PP27,218 P3
(45) Date of Patent: Sep. 27, 2016

(54) ***NEMESIA* PLANT NAMED 'EASTER BONNET'**

(50) Latin Name: *Nemesia foetens*
Varietal Denomination: Easter Bonnet

(71) Applicant: Martine Tellwright, Barnham (GB)

(72) Inventor: Martine Tellwright, Barnham (GB)

( * ) Notice: Subject to any disclaimer, the term of this patent is extended or adjusted under 35 U.S.C. 154(b) by 173 days.

(21) Appl. No.: 14/121,780

(22) Filed: Oct. 16, 2014

(65) Prior Publication Data

US 2016/0113185 P1 Apr. 21, 2016

(51) Int. Cl.
*A01H 5/02* (2006.01)

(52) U.S. Cl.
USPC ..... Plt./458

(58) Field of Classification Search
USPC ..... Plt./458
See application file for complete search history.

*Primary Examiner* — Keith Robinson
(74) *Attorney, Agent, or Firm* — Bethany R. Roahrig; Cochran Freund & Young, LLC

(57) ABSTRACT

A new *Nemesia* plant particularly distinguished by a prolific display of bi-colored flowers whose upper petal is soft lavender pink and lower petal is a contrasting cream white with a prominent orange-yellow eye, and strongly fragrant flowers, is disclosed.

2 Drawing Sheets

Genus and species: *Nemesia foetens.*
Variety denomination: 'Easter Bonnet'.

BACKGROUND

The present invention relates to a new and distinct cultivar of *Nemesia* plant grown as an ornamental for use in garden and landscape borders, or in containers. The new variety is known botanically as *Nemesia foetens* and will be referred to hereinafter by the variety name 'Easter Bonnet'.

'Easter Bonnet' resulted from a formal breeding program begun by the inventor in 1998 at her nursery in West Sussex, United Kingdom. The purpose of the breeding program is to produce new varieties of *Nemesia* that exhibit compact habit and new flower colors and color combinations.

In 2011, the inventor conducted a controlled cross-pollination between two unreleased and unpatented selections of *Nemesia* from the inventor's breeding program, namely *Nemesia* code number '1100' (unpatented) as the male parent and *Nemesia* code number '1156' (unpatented) as the female parent. 'Easter Bonnet' was selected by the inventor in 2012 for its attractive bi-colored flowers and prominent orange-yellow eye. In addition, 'Easter Bonnet' exhibits an upright compact rounded habit, medium-green leaves, and strongly fragrant flowers.

'Easter Bonnet' was first asexually propagated by the inventor in 2012 in an unheated greenhouse at the inventor's nursery in West Sussex, United Kingdom using softwood cuttings. The inventor has determined that 'Easter Bonnet' is stable and uniform, and reproduces true to type in successive generations of asexual reproduction via softwood cuttings.

SUMMARY

The following traits have been repeatedly observed and represent the distinguishing characteristics of 'Easter Bonnet'. 'Easter Bonnet' has not been tested under all possible conditions and phenotypic differences may be observed with variations in environmental, climatic, and cultural conditions, without however, any variance in genotype.

1. 'Easter Bonnet' exhibits a compact upright habit.
2. A 6 months old plant of 'Easter Bonnet' grown in a 9 cm container is 15 cm in height and 10-12 cm in width.
3. A 9 months old plant of 'Easter Bonnet' grown in a 13 cm container is 25-30 cm in height and 18-20 cm in width.
4. 'Easter Bonnet' exhibits bicolor flowers which have a soft lavender pink upper petal and a creamy white lower petal.
5. The flowers of 'Easter Bonnet' exhibit a prominent orange-yellow-colored palate or "eye".
6. 'Easter Bonnet' is floriferous.
7. 'Easter Bonnet' flowers are pleasantly fragrant with a vanilla scent.
8. 'Easter Bonnet' has a long blooming period, from early spring until fall.
9. 'Easter Bonnet' is hardy to −6° Celsius and survives in USDA Zone 9.

DESCRIPTION OF THE PHOTOGRAPHS

The accompanying color photographs illustrate the overall appearance of the new *Nemesia* cultivar 'Easter Bonnet' showing the colors as true as it is reasonably possible to obtain in colored reproductions of this type. The photographs were taken in April 2014.

DESCRIPTION OF THE NEW VARIETY

Figure 1:
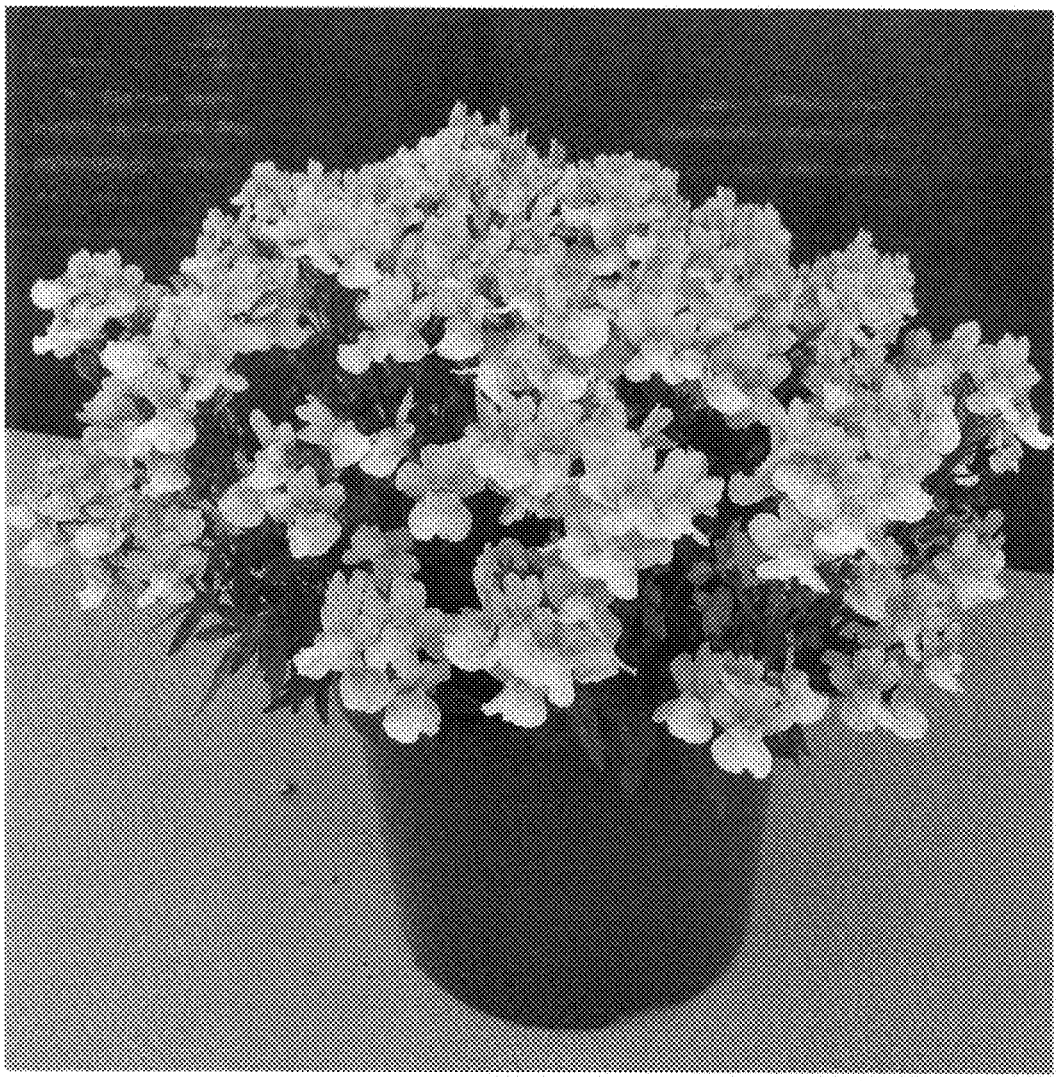
FIG. 1 shows a 9-month old plant grown from a cutting in a 1-liter container outdoors in Oxnard, Calif. The plant has been grown naturally, without the use of pinching or chemical growth regulator treatments.
Figure 2:
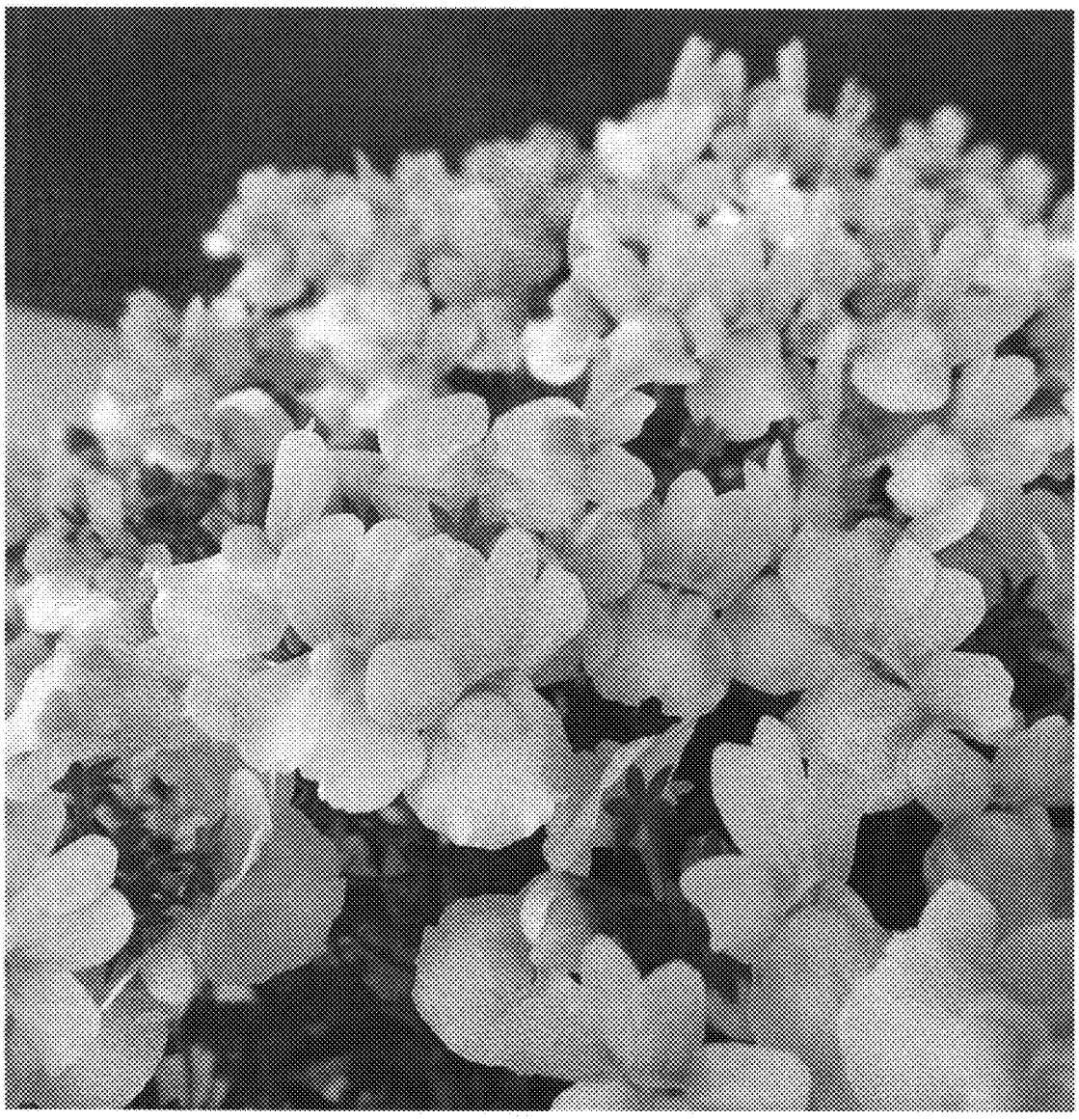
FIG. 2 depicts a close-up view of the flowers.

The following detailed descriptions set forth the distinctive characteristics of 'Easter Bonnet'. Observations, measurements, values, and comparisons were collected in August, 2014 in Santa Barbara, Calif. from a 9-month old plant grown outdoors in a 13 cm diameter container. Color determinations were made in accordance with The 2007 Royal Horticultural Society Colour Chart from London England.

Classification:

*Family*.—Plantaginaceae.

*Genus*.—*Nemesia*.

*Species*.—*foetens*.

*Common name*.—*Nemesia*.

Parentage:

*Female parent*.—*Nemesia* code number '1156' (unpatented).

*Male parent*.—*Nemesia* code number '1100' (unpatented).

Plant description:

*Growth habit*.—Upright, compact habit.

*Vigor*.—Vigorous.

*Plant dimensions*.—6-month old: 15 cm in height and 10 cm to 12 cm in width. 9-month old: 25 cm to 30 cm in height and 18 cm to 20 cm in width.

*Type*.—Perennial in USDA zones 9 and warmer; annual in zones colder than zone 9.

*Root system*.—Fine.

*Hardiness*.—Hardy to minus 6° Centigrade.

Propagation: Softwood cuttings.

*Time to initiate roots*.—Approximately 14 days are needed to develop roots on initial cuttings.

*Temperatures to initiate rooting*.—The air temperature that is recommended for rooting is 16° Centigrade and the soil temperature that is recommended for rooting is 24° Centigrade.

*Crop time*.—Approximately 8 weeks are needed to produce a finished 9 cm container plant from a rooted cutting.

*Special or recommended growing requirements*.—Pruning: Pinch back the growing tips when potting into the final growing container. Soil: 70% medium grade peat, 10% coarse peat and 20% 12 mm bark. Suggested commercial container size: 9 cm or 13 cm diameter containers. Cultural needs: Full sun, moist well-draining soil or peat-based medium, and application of a general plant fertilizer during the growing season.

Stems:

*Stem shape*.—Quadrate.

*Stem length*.—12 cm.

*Stem diameter*.—3 mm.

*Stem surface*.—Glabrous.

*Stem color*.—138B.

*Pubescence*.—Absent.

*Internode length*.—2.5 cm.

*Branching habit*.—Basal.

Foliage:

*Leaf arrangement*.—Opposite.

*Type*.—Evergreen.

*Leaf shape*.—Ovate.

*Leaf division*.—Simple.

*Leaf apex*.—Acute.

*Leaf base*.—Rounded.

*Leaf margins*.—Entire.

*Leaf surface* (*both surfaces*).—Glabrous.

*Leaf length*.—Fully developed, from 3.0 cm to 3.5 cm.

*Leaf width*.—12 mm to 15 mm.

*Leaf variegation*.—Absent.

*Leaf color*.—Upper surface: 138A. Lower surface: 138B.

*Leaf attachment*.—Predominately sessile.

*Vein pattern*.—Pinnate with mid-vein depressed on upper surface and protruding mid-vein on lower surface.

*Vein color* (*both surfaces*).—138C.

Petioles (when present):

*Petiole shape*.—Sulcate.

*Petiole surface*.—Glabrous.

*Petiole dimensions*.—1 mm to 4 mm in length and 2 mm in width.

*Petiole color*.—138B.

Inflorescence:

*Flowering season*.—Spring, summer, and fall in West Sussex, United Kingdom. Flowers repeatedly through the year, flowers are bicolored lavender pink and cream-white in color. The flowers also exhibit a prominent orange-yellow eye, 13A becoming 12A as the flower ages.

*Fragrance*.—Strong vanilla fragrance.

*Self-cleaning or persistent*.—Markedly self-cleaning.

*Type of inflorescence*.—Terminal racemes. Length: 4 cm. Width: 4 cm. Quantity per plant: Approximately 100 to 120 racemes. Quantity of flowers per raceme: A range of 18 to 20 flowers and buds. Lastingness of individual flower on the plant: An individual flower lasts 7 to 10 days.

Flower buds:

*Surface*.—Glabrous.

*Height*.—3 mm.

*Diameter*.—5 mm.

*Shape*.—Ovoid.

*Color*.—NN155D (as petals first emerge).

Peduncle:

*Length*.—4 cm to 5 cm.

*Diameter*.—2 mm.

*Shape*.—Quadrate.

*Texture*.—Glabrous.

*Color*.—138B.

Flower description:

*Flower shape*.—Personate.

*Flower dimensions*.—Height: 21 mm. Width: 17 mm. Depth: 8 mm.

*Pedicel*.—Length: 12 to14 mm. Diameter: less than 1 mm. Shape: Closest to cylindrical with one longitudinal furrow. Texture: Glabrous. Color: 138B.

*Petals*.—Corolla: Tube pouch and spur attached to base. Corolla tube dimensions: 4 mm in length and 3 mm in diameter. Corolla tube color (inner and outer surfaces): NN155D. Corolla tube color change with age: Absent. Upper petal: Color: Upper surface: Ranges between 75A (newly open) and 85C (lavender pink) at 7-10 days. Lower surface: NN155D (cream-white). Length: 15 mm. Width: 18 mm. Margins: Entire. Apex: Rounded. Texture (both surfaces): Glabrous Lobes: Number: 4, basally fused. Outer lobes: 5 mm in width, 9 mm in length. Inner lobes: 4 mm in width, 9 mm in length. Pollinator guide lines: Approximately 15 parallel fine guide lines 3 mm to 5 mm in length, 92A in color. Lower petal: Color (both surfaces): Ranges between 4C (yellow) and NN155B (cream-white). Length: 10 mm. Width: 14 cm. Margins: Entire. Apex: Emarginate. Texture (both surfaces): Glabrous.

*Sepals*.—Calyx: Diameter: 7 mm. Depth: 1.5 mm. Shape: Stellate. Quantity: 5, basally fused. Sepal texture (both surfaces): Pubescent. Sepal apex: Acute. Sepal shape: Lanceolate. Sepal dimensions: 3 mm in length and 1.5 mm in width. Sepal margin: Entire. Sepal color (both surfaces): 138B. Palate color: 13A becoming 12A as flower ages. Palate dimensions: 3 mm in length and 3 mm in width. Nectary guide: Absent. Nectary throat (appears as pouch externally): Width at base of flower: 4 mm. Color: Interior: 160A. Exterior: 160C. Nectary funnel (appears as spur externally): Length: 4 mm. Diameter: 1 mm. Color (both surfaces): 160C. Nectary surface: Smooth, semi-glossy.

Reproductive organs:

*Stamens*.—Number: 4. Two discrete: Length: 4 mm Diameter: 0.5 mm nearer, 3 mm from upper petal base. Two rudimentary: Length: less than 0.5 mm. Diameter: 0.6 mm from upper petal base. Color: 155C. Anther: Color: 163B. Length: 0.50 mm. Width: 0.50 mm. Pollen: None observed.

*Pistil*.—Ovary: Shape: Ovoid. Length: 1.25 mm. Diameter: 1 mm. Color: 141C. Surface: Glossy. Pistil number: One, rudimentary, appears as tiny stub. Pistil color: 155C.

Fruit/seed set: None observed.

Disease and pest susceptibility: 'Easter Bonnet' is susceptible to aphid-transmitted viruses Impatiens Necrotic Spot Virus (INSV) and Tomato Spotted Wilt Virus (TSWV). Both INSV and TSWV are classified in the genus *Tospovirus*. 'Easter Bonnet' is susceptible to chlorosis (yellowing of the foliage) when colonized by greenhouse whitefly (*Trialeurodes vaporariorum*).

COMPARISON WITH PARENTAL LINES AND KNOWN VARIETY

'Easter Bonnet' is distinguishable from the male parent, '1100' (unpatented) as follows: whereas the flowers of 'Easter Bonnet' are bi-colored exhibiting a soft lavender pink upper petal and a cream white colored lower petal, with an orange-yellow eye, the flowers of the male parent exhibit a pink upper petal and pale yellow lower petal. Additionally 'Easter Bonnet' exhibits an upright compact habit with strongly fragrant flowers, whereas '1100' has a more open, less compact habit and significantly less scented flowers.

'Easter Bonnet' is distinguishable from the female parent, '1156' (unpatented) as follows: whereas the flowers of 'Easter Bonnet' are bi-colored with a soft lavender pink upper petal and a cream white colored lower petal, with an orange-yellow eye, the flowers of the female parent are entirely mauve in color. Additionally, '1156' exhibits a dwarf habit, growing to an average of 15 cm at maturity while 'Easter Bonnet' averages 25 to 30 cm at maturity.

The closest comparison plant known to the inventor is the inventor's variety, 'FLEURIPI' (U.S. Plant Pat. No. 16,851). 'FLEURIPI' is distinguishable from 'Easter Bonnet' as follows: Mature plants of 'FLEURIPI' are shorter in height than plants of 'Easter Bonnet'. 'FLEURIPI' has strong pink colored flowers compared to 'Easter Bonnet' which has bi-colored flowers with a soft lavender pink upper petal and a cream white colored lower petal, with a prominent orange-yellow eye.

I claim:

1. A new and distinct cultivar of *Nemesia* plant named 'Easter Bonnet' as described and illustrated herein.

* * * * *